(12) United States Patent
Vlachos

(10) Patent No.: US 8,632,602 B2
(45) Date of Patent: Jan. 21, 2014

(54) HIP RESURFACING IMPLANT

(76) Inventor: Ioannis Vlachos, Attikis (GR)

(*) Notice: Subject to any disclaimer, the term of this patent is extended or adjusted under 35 U.S.C. 154(b) by 1034 days.

(21) Appl. No.: 12/085,989

(22) PCT Filed: Dec. 5, 2006

(86) PCT No.: PCT/GR2006/000066
§ 371 (c)(1),
(2), (4) Date: Jun. 4, 2008

(87) PCT Pub. No.: WO2007/066156
PCT Pub. Date: Jun. 14, 2007

(65) Prior Publication Data
US 2009/0048681 A1 Feb. 19, 2009

(30) Foreign Application Priority Data
Dec. 5, 2005 (GR) .................................. 050100593

(51) Int. Cl.
*A61F 2/36* (2006.01)
(52) U.S. Cl.
USPC ..................................... 623/23.14; 623/23.12
(58) Field of Classification Search
USPC .......... 623/22.15–22.17, 22.21, 22.32, 22.34, 623/22.35, 23.12–23.14, 23.36, 23.37
See application file for complete search history.

(56) References Cited

U.S. PATENT DOCUMENTS

| 4,035,848 A | 7/1977 | Wagner |
| 5,725,593 A | 3/1998 | Caracciolo |
| 2003/0130741 A1* | 7/2003 | McMinn .................... 623/23.14 |
| 2003/0163202 A1* | 8/2003 | Lakin ........................ 623/22.15 |

FOREIGN PATENT DOCUMENTS

| CH | 626249 | 11/1981 |
| DE | 3017953 | 2/1981 |
| GB | 2007980 | 5/1979 |

* cited by examiner

*Primary Examiner* — David H Willse
*Assistant Examiner* — Javier Blanco
(74) *Attorney, Agent, or Firm* — Andrew C Aitken

(57) ABSTRACT

An implant meant for hip resurfacing arthroplasty, a surgical reconstruction performed on patients with diseased hips, during which the surgeon replaces the surface of the femoral head with a polished metallic hemispherical shell is disclosed. The implant includes a metallic shell with a polished hemispherical outer surface and an inner hemispherical concave surface, from which extends a trunnion having internal threads and thin meridian fins. The inner concave surface of the implant is fully metal porous coated for osseointegration between implant and bone. The presented implant is fitted onto the appropriately contoured femoral head and is stabilized by means of a preload tension wire which drills the femoral head and neck and exits the greater trochanter. The wire attaches proximally to the thread of the trunnion of the shell and distally to a nut-washer combination, by the tightening of which establishment of preload is achieved.

4 Claims, 1 Drawing Sheet

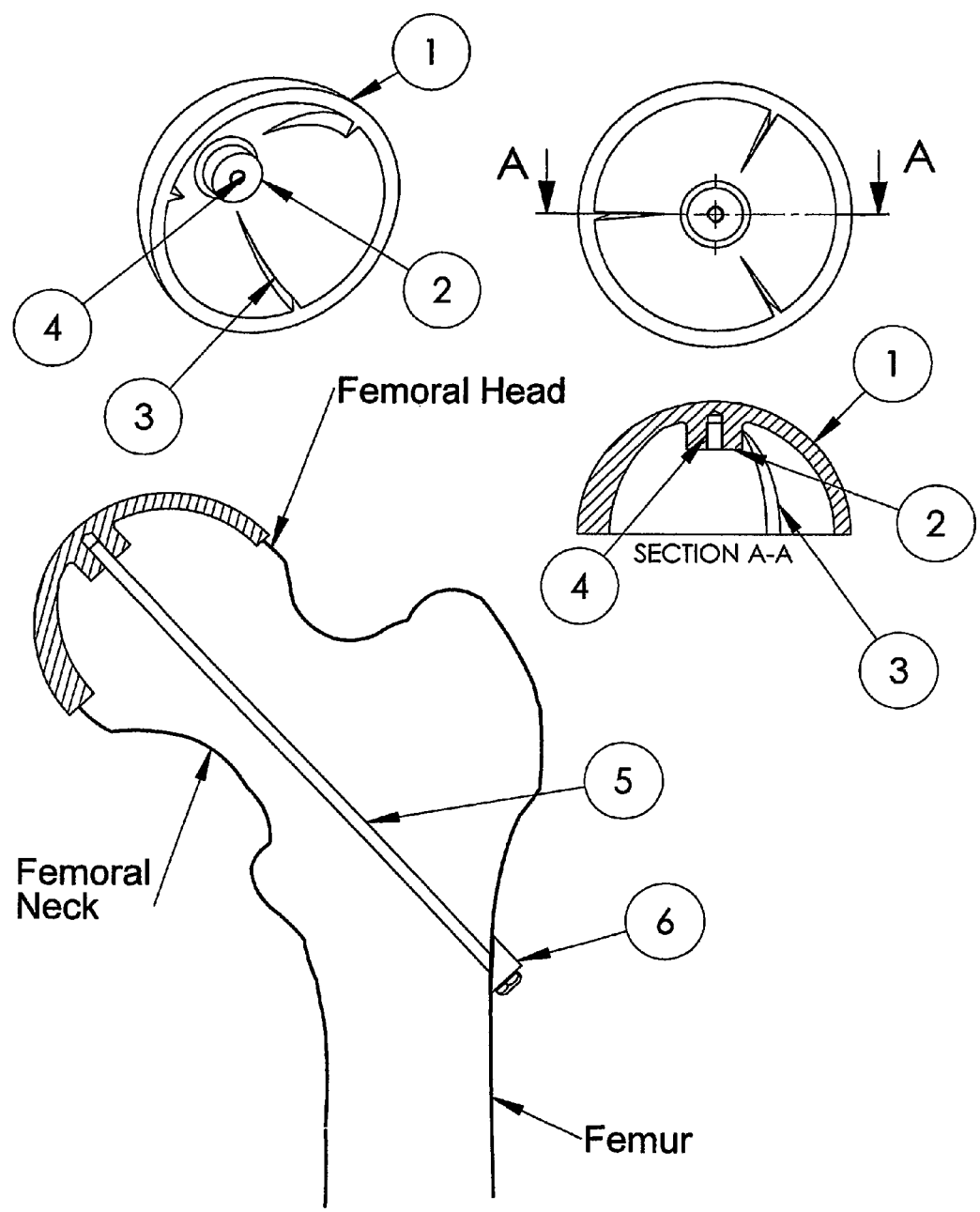

HIP RESURFACING IMPLANT

The presented invention is an implant meant for hip resurfacing arthroplasty, a surgical reconstruction performed on patients with diseased hip joint.

Patients with diseased hip joints (e.g. osteoarthritis) are usually subjected to total hip replacement, in order to provide pain relief and ensure functional rehabilitation of the joint. During such reconstructive procedures the acetabulum of the pelvis as well as the upper part of the femur (neck and head) are replaced with appropriate implants assembled by means of polished spherical bearing surfaces.

In some cases however, it is clinically possible to preserve the femoral neck and head and limit surgical reconstruction to the replacement of the femoral head bearing surface (hip resurfacing arthroplasty). This is implemented by means of a polished metallic implant, which geometrically resembles a thin-walled spherical shell, fixed against the appropriately contoured femoral head.

Currently available hip resurfacing implants demonstrate the following disadvantages:

The external surface of the polished shell is part of a sphere exceeding north hemisphere by 20+20 or even 30+30 degrees of south latitude beyond the equator. As a result, the circumferential rim of the shell is relatively limited, making fitting onto the femoral head impossible with minor peripheral contouring of the femoral head. Therefore, in order to fit such shells major peripheral bone removal is necessary, to an extent that the contoured femoral head finally approaches the profile of its initially narrower femoral neck. This compromises the strength of the anatomic region, usually resulting in postoperative complications related to fracture of the femoral neck due to increased stresses.

Furthermore, currently available hip resurfacing implants ensure fixation by means of an inner central peg, sized up to 10 mm in cross-sectional diameter, for the insertion of which further bone removal is necessary by means of equivalent femoral head and neck drilling. This reduces the strength of the anatomic region even more and simultaneously affects local vascularization.

Furthermore, currently available hip resurfacing implants are fixed by means of acrylic resin cement, which is meant to ensure bonding between the metallic shell and the exposed cancellous bone of the contoured femoral head. During the exothermic reaction of cement polymerization however, the integrity of the underlying cancellous bone is further compromised.

The presented invention is an implant meant for hip resurfacing arthroplasty which effectively addresses the above mentioned disadvantages of currently available implants and on the same time introduces some advantages important for the biomechanics of the anatomic region under study. The presented implant consists of: the main component which is a polished metallic shell, a preload tension wire and a nut with washer. All components are shown in the attached drawing.

The metallic shell (1) of the presented implant is a thin-walled spherical shell of 180 degrees (exactly hemispherical) with a polished outer (convex) surface. The inner (concave) surface of the metallic shell is also hemispherical. This offers an important benefit in that the circumferential rim of the shell is maximum; thus making fitting onto the femoral head possible with minor peripheral contouring, avoiding significant bone removal.

Furthermore, the metallic shell (1) of the presented implant possesses on the pole of the inner (concave) surface a short trunnion (2). This offers an important benefit in that no extensive drilling is necessary deep along the femoral head and neck, thus preserving integrity of underlying bone and local vascularization.

Furthermore, the metallic shell (1) of the presented implant possesses on the inner (concave) surface thin meridian fins (3), while on the centre of the short trunnion there is a female thread (4) meant for attachment of the preload tension wire. By these two means (fins and preload), immediate postoperative torsional and axial stability are adequately ensured, thus making use of bonding acrylic resin cement obsolete. For the purpose of longterm implant stability, the inner surface of the metallic shell is metal porous coated, which under the favorable effect of preload, leads to permanent osseointegration on the underlying bone.

The entire length of the preload tension wire (5) of the presented implant possesses a thread equivalent to the female one of the trunnion. One end of the preload tension wire (5) is trocar. Thus, while one end of the preload tension wire can be screwed in the trunnion, the trocar end can, by drilling the femoral head and neck along the appropriate direction, be stabilized at the region of the greater trochanter by means of the nut-washer combination (6). It is then possible to finally apply the necessary preload on the wire.

During the course of a surgical hip resurfacing procedure, use of the presented implant is accomplished by the following steps:

a) Drilling of the femoral head and neck by means of the preload tension wire all the way to the greater trochanter, along a direction derived by appropriate preoperative planning. Distally the wire exits the femur projecting beyond the greater trochanter, while proximally is prevented from fully inserting.

b) The wire remains in place and is then used as a centralizer guide for the necessary processes of minor head contouring and trunnion recess milling, according to the size of the presented implant.

c) Complete attachment of the metallic shell on the threaded wire and subsequent traction of the wire (with the attached shell) from the side of the greater trochanter.

d) Use of the nut-washer combination to safely lock the distally protruding part of the wire against the cortex of the greater trochanter.

e) Tightening of the nut-washer combination, which simultaneously imposes the following: subsidence of the metallic shell onto the contoured femoral head, embedment of inner meridian fins on the underlying bone and finally establishment of required preload along the tension wire.

f) Cutting away the wire part which extends beyond the nut after establishment of preload.

The presented hip resurfacing implant effectively addresses the disadvantages of currently available ones, preserving significantly more and better vascularized underlying bone on the femoral head and neck sites. At the same time, the presented implant introduces the advantage of preload, which favours immediate postoperative implant stability, without disturbing the longterm biomechanics of the region, but in contrary enhancing the strength of the bony femoral neck.

The invention claimed is:

1. A hip resurfacing implant, comprising a shell section, a wire and an attachment means to attach said secure said wire at a distal location opposite said shell section, said shell section comprised of a which is metallic material and geometrically part of a thin-walled hemispherical shell and further adapted to fit against an appropriately contoured femoral head, said hemispherical shell being characterized by a convex polished smooth continuously curved surface that is hemispherical and said hemispherical shell is further adapted to be affixed to underlying bone by said wire, said wire adapted to attach proximally to and extend from a trunnion that is provided at an antipodal point of said hemispherical shell projecting from the concave interior surface of said shell and said wire having a length to allow it to extend through the femoral head and through the femoral neck and exit the femur through the greater trochanter and said attachment means attaches to said wire distally from said shell and comprises a nut-washer combination whereby the tightening of said nut establishes a preload.

2. A hip resurfacing, implant according to claim 1, further comprising thin meridian fins extending from the inner concave surface of said shell and a metal porous coating for the purpose of osseointegration between implant and underlying bone on said inner concave surface.

3. The hip resurfacing implant recited in claim 1 wherein said wire is attached to said trunnion by engagement of opposite threads.

4. The hip resurfacing implant recited in claim 1 wherein said trunnion is integral with said shell, and said trunnion extends from an interior surface of said shell in an axial direction a distance less than the radial distance of the circle formed by the hemispherical opening of said shell.

\* \* \* \* \*